US007285381B1

(12) United States Patent
Hallek et al.

(10) Patent No.: US 7,285,381 B1
(45) Date of Patent: Oct. 23, 2007

(54) SCLEROPROTEIN OF AN ADENO-ASSOCIATED VIRUS WITH MODIFIED CHROMATOGRAPHIC PROPERTIES, THE PRODUCTION THEREOF AND USE OF THE SAME

(75) Inventors: Michael Hallek, Schondorf (DE); Anne Girod, München (DE); Martin Ried, Sinning (DE); Christof Körner, München (DE); Ulrich Moebius, Gauting-Unterbrunn (DE)

(73) Assignee: MediGene Aktiengesellschaft, Planegg/Martinsried (DE)

( * ) Notice: Subject to any disclaimer, the term of this patent is extended or adjusted under 35 U.S.C. 154(b) by 662 days.

(21) Appl. No.: 10/031,187

(22) PCT Filed: Jul. 18, 2000

(86) PCT No.: PCT/EP00/06861

§ 371 (c)(1),
(2), (4) Date: Jun. 12, 2002

(87) PCT Pub. No.: WO01/05991

PCT Pub. Date: Jan. 25, 2001

(30) Foreign Application Priority Data

Jul. 19, 1999 (DE) ............................. 199 33 719

(51) Int. Cl.
C12Q 1/70 (2006.01)
C12P 19/34 (2006.01)
C12N 7/04 (2006.01)
C12N 7/02 (2006.01)

(52) U.S. Cl. ................. 435/5; 435/91.33; 435/236
(58) Field of Classification Search .................. 435/5, 435/173.3, 320.1, 239, 475; 530/412, 413
See application file for complete search history.

(56) References Cited

U.S. PATENT DOCUMENTS 5,276,136 A * 1/1994 Skubitz et al. .............. 530/326
6,491,907 B1 * 12/2002 Rabinowitz et al. ....... 424/93.2
2001/0031463 A1 10/2001 Kleinschmidt et al.
2002/0192823 A1 12/2002 Bartlett

FOREIGN PATENT DOCUMENTS

| WO | WO95/23867 | 9/1995 |
| WO | WO 95/23867 | 9/1995 |
| WO | WO 96/00587 | 1/1996 |
| WO | WO96/00587 | 1/1996 |
| WO | WO97/08298 | 3/1997 |
| WO | WO 97/38723 | 10/1997 |
| WO | WO97/38723 | 10/1997 |
| WO | WO99/67393 | 12/1999 |
| WO | WO 99/67393 | 12/1999 |

OTHER PUBLICATIONS

Hoque et al., Chimeric Virus-like Particle Formation of Adeno-Associated Virus (Biochemical and Biophysical Research Communications 266, 371-376, 1999.*
Yang et al., Developemant of Novel Cell Surface CD34-Targeted Recombinant Adenoassociated Virus Vectors for Gene Therapy (Human Gene Therapy 9:1929-1937, Sep. 1, 1998.*
Spear et. al., Evidence for Two Nucleotide Sequences Orientations within the Terminal Repetition of Adeno-Associated Virus DNA (Journal of Virology, Nov. 1977, p. 627-634).*
Ruffing et al., Mutations in the carboxy trminus of adeno-associated virus 2 capsid proteins affect viral infectivity: lack of an RGD integrin-binding motif. (Journal of General Virology, Dec. 1994;75 (Pt 12):3385-3392).*
Wistuba et al., "Intermediates of Adeno-Associated Virus Type 2 Assembly: Identification of Soluble Complexes Containing Rep and Cap Proteins," *Journal of Virology* 69:5311-5319 (1995).
Aumailley et al., "Identification of the Arg-Gly-Asp Sequence in Laminin A Chain as a Latent Cell-Binding Site Being Exposed in Fragment P1," *FEBS* 262:82-86 (1990).
Bartlett et al., "Targeted Adeno-Associated Virus Vector Transduction of Nonpermissive Cells Mediated by a Bispecific F (ab'γ)$_2$ Antibody," *Nature Biotechnology* 17:181-186 (1999).
Chiorini et al., "High-Efficiency Transfer of the T Cell Co-Stimulatory Molecule B7-2 to Lymphoid Cells Using High Titer Recombinant Adeno-Associated Virus Vectors," *Human Gene Therapy* 6:1531-1541 (1995).
Cosset et al., "Targeting Retrovirus Entry," *Gene Therapy* 3:946-956 (1996).
Douglas et al., "Targeted Gene Delivery by Tropism-Modified Adenoviral Vectors," *Nature Biotechnology* 14:1574-1578 (1996).
Girod et al., "Genetic Capsid Modifications Allow Efficient Re-Targeting of Adeno-Associated Virus Type 2," *Nature Medicine* 5:1052-1056 (1999).
Hermonat et al., "Genetics of Adeno-Associated Virus: Isolation and Preliminary Characterization of Adeno-Associated Virus Type 2 Mutants," *Journal of Virology* 51:329-339 (1984).
Kotin, "Prospects for the Use of Adeno-Associated Virus as a Vector for Human Gene Therapy," *Human Gene Therapy* 5:793-801 (1994).
Krasnykh et al., "Generation of Recombinant Adenovirus Vectors with Modified Fibers for Altering Viral Tropism," *Journal of Virology* 70:6839-6846 (1996).
Luo, "Preliminary X-Ray Crystallographic Analysis of Canine Parvovirus Crystals," *J. Mol. Biol.* 200:209-211 (1988).
Muzyczka, "Use of Adeno-Associated Virus as a Genaral Transduction Vector for Mammalian Cells," *Current Topics in Microbiology and Immunology* 158:98-129 (1992).

(Continued)

Primary Examiner—Bruce R. Campell
Assistant Examiner—Sharon Hurt
(74) Attorney, Agent, or Firm—Clark & Elbing LLP (57) ABSTRACT

The invention relates to a scleroprotein of an adeno-associated virus which contains at least one mutation. Said mutation causes the chromatographic properties to be modified. The invention also relates to the production of said scleroprotein and the use thereof.

28 Claims, 2 Drawing Sheets

OTHER PUBLICATIONS

Ohno et al., "Cell-Specific Targeting of Sindbis Virus Displaying IgG-Binding Domains of Protein A," *Nature Biotechnology* 5:763-767 (1997).
Ruffing et al., "Mutations in the Carboxy Terminus of Adeno-Associated Virus 2 Capsid Proteins Affect Viral Infectivity: Lack of an RGD Integrin-Binding Motif," *Journal of General Virology* 75:3385-3392 (1994).
Ruffing et al., "Assembly of Viruslike Particles by Recombinant Structural Proteins of Adeno-Associated Virus Type 2 in Insect Cells," *Journal of Virology* 66:6922-6930 (1992).
Rutledge et al., "Infectious Clones and Vectors Derived From Adeno-Associated Virus (AAV) Serotypes Other Than AAV Type 2," *Journal of Virology* 72:309-319 (1998).
Srivastava et al., "Nucleotide Sequence and Organization of the Adeno-Associated Virus 2 Genome," *Journal of Virology* 45:555-564 (1983).
Steinbach et al., "Assembly of Adeno-Associated Virus Type 2 Capsids in Vitro," *Journal of General Virology* 78:1453-1462 (1997) (Abstract).
Valsesia-Wittmann et al., "Modifications in the Binding Domain of Avian Retrovirus Envelope Protein To Redirect the Host Range of Retroviral Vectors," *Journal of Virology* 68:4609-4619 (1994).
Wickham et al., "Increased in Vitro and In Vivo Gene Transfer by Adenovirus Vectors Containing Chimeric Fiber Proteins," *Journal of Virology* 71:8221-8229 (1997).
Wistuba et al., "Subcellular Compartmentalization of Adeno-Associated Virus Type 2 Assembly," *Journal of Virology* 71:1341-1352 (1997).
Wu et al., "The Canine Parvovirus Empty Capsid Structure," *Mol. Biol.* 233:231-244 (1993).
Yang et al., "Development of Novel Cell Surface CD34-Targeted Recombinant Adenoassociated Virus Vectors for Gene Therapy," *Human Gene Therapy* 9:1929-1937 (1998).
Chapman et al., "Structure, Sequence, and Function Correlations Among Parvoviruses," *Virology* 194:491-508 (1993).
Luo et al., "Preliminary X-Ray Crystallographic Analysis of Canine Parovirus Crystals," *J. Mol. Biol.* 200:209-211 (1988).
Muzyczka, "Use of Adeno-Associated Virus as a General Transduction Vector for Mammalian Cells," *Current Topics in Microbiology and Immunology* 158:97-129 (1992).
Nimako et al., "Human Papillomavirus-Specific Cytotoxic T Lymphocytes in Patients with Cervical Intraepithelial Neoplasia Grade III," *Cancer Research* 57:4855-4861 (1997).
Steinbach et al., "Assembly of Adeno-Associated Virus Type 2 Capsids in vitro," *Journal of General Virology* 78:1453-1462 (1997) (Abstract).
Stevenson et al., "Selective Targeting Human Cells by a Chimeric Adenovirus Vector Containing a Modified Fiber Protein," *Journal or Virology* 71:4782-4790 (1997).
Tarpey et al., "Human Cytotoxic T Lymphocytes Stimulated by Endogenously Processed Human Papillomavirus Type 11 E7 Recognize a Peptide Containing a HLA-A2 (A*0201) Motif," *Immunology* 81:222-227 (1994).
Tsao et al., "The Three-Dimensional Structure of Canine Parvovirus and Its Functional Implications," *Science* 251:1456-1464 (1991).
Wickham et al., (1996), "Adenovirus Targeted to Heparan-containing Receptors Increases its Gene Delivery Efficiency to Multiple Cell Types," *Nat. Biotechnol.*, 14:1570-1573.
Wu et al., "The Canine Parvovirus Empty Capsid Structure," *J. Mol. Biol.* 233:231-244 (1993).
Anderson, "Human Gene Therapy," *Nature* 392:25-30 (1998).
Asokan et al., "AAV Does the Shuffle," *Nature Biotechnology* 24:158-160 (2006).
Buning et al., "Receptor Targeting of Adeno-Associated Virus Vectors," *Gene Therapy* 10:1142-1151 (2003).
Grifman et al., Incorporation fo Tumor-Targeting Peptides into Recombinant Adeno-Associated Virus Capsids, *Molecular Therapy* 3:964-975 (2001).
Hoque et al., "Nuclear Transport of the Major Capsid Protein is Essential for Adeno-Associated Virus Capsid Formation," *Journal of Virology* 73:7912-7915 (1999).
Huttner et al., "Genetic Modifications of the Adeno-Associated Virus Type 2 Capsid Reduce the Affinity and the Neutralizing Effects of Human Serum Antibodies," *Gene Therapy* 10:2139-2147 (2003).
Kmiec, "Gene Therapy," *American Scientist* 87:240-247 (1999 ).
Maass et al., "Recombinant Adeno-Associated Virus for the Generation of Autologous, Gene-Modified Tumor Vaccines: Evidence for a High Transduction Efficiency into Primary Epithelial Cancer Cells," *Human Gene Therapy* 9:1049-1059 (1998).
Maheshri et al., "Directed Evolution of Adeno-Associated Virus Yields Enhanced Gene Delivery Vectors," *Nature Biotechnology* 24:198-204 (2006).
Marshall, "Second Child in French Trial is Found to Have Leukemia," *Science* 299:320 (2003).
Meng et al., "Tumor Suppressor Genes as Targets for Cancer Gene Therapy," *Gene Therapy of Cancer* Chapter 1, pp. 3-18 (1999).
Mizukami et al., "Adeno-Associated Virus Type 2 Binds to a 150-Kilodalton Cell Membrane Glycoprotein," *Virology* 217:124-130 (1996).
Moskalenko et al., "Epitope Mapping of Human Anti-Adeno-Associated Virus Type 2 Neutralizing Antibodies: Implications for Gene Therapy and Virus Structure," *Journal of Virology* 74:1761-1766 (2000).
Nicklin et al., "Efficient and Selective AAV2-Mediated Gene Transfer Directed to Human Vascular Endothelial Cells," *Molecular Therapy* 4:174-181 (2001).
Perabo et al., "In Vitro Selection of Viral Vectors with Modified Tropism: The Adeno-Associated Virus Display," *Molecular Therapy* 8:151-157 (2003).
Qing et al., "Human Fibroblast Growth Factor Receptor 1 is a Co-Receptor for Infection by Adeno-Associated Virus 2," *Nature Medicine* 5:71-77 (1999).
Ried et al., "Adeno-Associated Virus Capsids Displaying Immunoglobulin-Binding Domains Permit Antibody-Mediated Vectors Retargeting to Specific Cell Surface Receptors," *Journal of Virology* 76:4559-4566 (2002).
Russell," Replicating Vectors for Gene Therapy of Cancer: Risks, Limitations and Prospects," *European Journal of Cancer* 30A:1165-1171 (1994).
Shi et al., "Insertional Mutagenesis of the Adeno-Associated Virus Type 2 (AAV2) Capsid Gene and Generation of AAV2 Vectors Targeted to Alternative Cell-Surface Receptors," *Human Gene Therapy* 12:1697-1711 (2001).
Shi et al., "RGD Inclusion of VP3 Provides Adeno-Associated Virus Type 2 (AAV2)-Based Vectors with a Heparan Sulfate-Independent Cell Entry Mechanism," *Molecular Therapy* 7:515-525 (2003).
Smith et al., "The Challenges of genome Sequence Annotation or the Devil is in the Details," *Nature Biotechnology* , 15:1222-1223 (1997).
Spear et al., "Evidence for Two Nucleotide Sequence Orientations Within the Terminal Repetition of Adeno-Associated Virus DNA," *Journal of Virology* 24:627-634 (1977).
Starovasnik et al., "Structural Mimicry of a Native Protein by a Minimized Binding Domain," *Proc. Natl. Acad. Sci. USA* 94:10080-10085 (1997).
Summerford et al., "Membrane Associated Heparan Sulfate Proteoglycan is a Receptor for Adeno-Associated Virus Type 2 Virions," *Journal of Virology* 72:1438-1445 (1998).
Summerford et al., "αVβ5 Integrin: A Co-receptor for Adeno-Associated Virus Type 2 Infection," *Nature Medicine* 5:78-82 (1999).
Tseng et al., "Evolutionary Model for Predicting Protein Function by Matching Local Surfaces: a Bayesian Monte Carlo Approach," The Ninth Annual Conference on Research in Computational Molecular Biology, May 14-18, 2005.
Verma et al., "Gene Therapy-Promises, Problems and Prospects," *Nature* 389:239-242 (1997).
Wendtner et al., "Efficient Gene Transfer of CD40 Ligand into Primary B-CLL cells using recombinant Adeno-Associated Virus (rAAV) Vectors," *Blood* 100:1655-1661 (2002).
White et al., "Designer Gene Therapy May Target Specific Body Area," *Business News* 2:1-2 (2003).

White et al., "Targeted Gene Delivery to Vascular Tissue in Vivo by Tropism-Modified Adeno-Associated Virus Vectors," *Circulation* 109:513-519 (2004).

Wobus et al., "Monoclonal Antibodies Against the Adèno-Associated Virus Type 2 (AAV-2) Capsid: Epitope Mapping and Identification of Capsid Domains Involved in AAV-2 Cell Interaction and Neutralization of AAV-2 Infection," *Journal of Virology* 74:9281-9293 (2000).

Wu et al., "Mutational Analysis of the Adeno-Associated Virus Type 2 (AAv2) Capsid Gene and Construction of AAV2 Vectors with Altered Tropism," *Journal of Virology* 74:8635-8647 (2000).

U.S. Appl. No. 60/123,651, "Adeno-Associated Virus Vectors and Methods of Making the Same," filed Mar. 10, 1999.

U.S. Appl. No. 60/107,840, "Adeno-Associated Virus Vectors and Methods of Making the Same," filed Nov. 10, 1998.

* cited by examiner

Fig. 1

Fig. 2

SEQUENCE LISTING

<160> NUMBER OF SEQ ID NOS: 18

<210> SEQ ID NO 1
<211> LENGTH: 14
<212> TYPE: PRT
<213> ORGANISM: Homo sapiens

<400> SEQUENCE: 1

Gln Ala Gly Thr Phe Ala Leu Arg Gly Asp Asn Pro Gln Gly
1               5                   10

<210> SEQ ID NO 2
<211> LENGTH: 10

```
<212> TYPE: PRT
<213> ORGANISM: adeno-associated virus

<400> SEQUENCE: 2

Tyr Lys Gln Ile Ser Ser Gln Ser Gly Ala
 1               5                   10

<210> SEQ ID NO 3
<211> LENGTH: 10
<212> TYPE: PRT
<213> ORGANISM: adeno-associated virus

<400> SEQUENCE: 3

Tyr Leu Thr Leu Asn Asn Gly Ser Gln Ala
 1               5                   10

<210> SEQ ID NO 4
<211> LENGTH: 10
<212> TYPE: PRT
<213> ORGANISM: adeno-associated virus

<400> SEQUENCE: 4

Tyr Tyr Leu Ser Arg Thr Asn Thr Pro Ser
 1               5                   10

<210> SEQ ID NO 5
<211> LENGTH: 10
<212> TYPE: PRT
<213> ORGANISM: adeno-associated virus

<400> SEQUENCE: 5

Glu Glu Lys Phe Phe Pro Gln Ser Gly Val
 1               5                   10

<210> SEQ ID NO 6
<211> LENGTH: 5
<212> TYPE: PRT
<213> ORGANISM: adeno-associated virus

<400> SEQUENCE: 6

Asn Pro Val Ala Thr
 1               5

<210> SEQ ID NO 7
<211> LENGTH: 5
<212> TYPE: PRT
<213> ORGANISM: adeno-associated virus

<400> SEQUENCE: 7

Glu Gln Tyr Gly Ser
 1               5

<210> SEQ ID NO 8
<211> LENGTH: 10
<212> TYPE: PRT
<213> ORGANISM: adeno-associated virus

<400> SEQUENCE: 8

Leu Gln Arg Gly Asn Arg Gln Ala Ala Thr
 1               5                   10

<210> SEQ ID NO 9
<211> LENGTH: 10
<212> TYPE: PRT
<213> ORGANISM: adeno-associated virus
```

-continued

```
<400> SEQUENCE: 9

Asn Val Asp Phe Thr Val Asp Thr Asn Gly
1               5                   10

<210> SEQ ID NO 10
<211> LENGTH: 10
<212> TYPE: PRT
<213> ORGANISM: Artificial Sequence
<220> FEATURE:
<223> OTHER INFORMATION: mutated VP3 of adeno-associated virus

<400> SEQUENCE: 10

Tyr Lys Gln Ile Ser Ser Gln Ser Gly Ala
1               5                   10

<210> SEQ ID NO 11
<211> LENGTH: 10
<212> TYPE: PRT
<213> ORGANISM: Artificial Sequence
<220> FEATURE:
<223> OTHER INFORMATION: mutated VP3 of adeno-associated virus

<400> SEQUENCE: 11

Tyr Leu Thr Leu Asn Asn Gly Ser Gln Ala
1               5                   10

<210> SEQ ID NO 12
<211> LENGTH: 10
<212> TYPE: PRT
<213> ORGANISM: Artificial Sequence
<220> FEATURE:
<223> OTHER INFORMATION: mutated VP3 of adeno-associated virus

<400> SEQUENCE: 12

Tyr Tyr Leu Ser Arg Thr Asn Thr Pro Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: mutated VP3 of adeno-associated virus

<400> SEQUENCE: 13

Glu Glu Lys Phe Phe Pro Gln Ser Gly Val
1               5                   10

<210> SEQ ID NO 14
<211> LENGTH: 10
<212> TYPE: PRT
<213> ORGANISM: Artificial Sequence
<220> FEATURE:
<223> OTHER INFORMATION: mutated VP3 of adeno-associated virus

<400> SEQUENCE: 14

Asn Pro Val Ala Thr Glu Gln Tyr Gly Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: mutated VP3 of adeno-associated virus
```

-continued

```
<400> SEQUENCE: 15

Leu Gln Arg Gly Asn Arg Gln Ala Ala Thr
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: mutated VP3 of adeno-associated virus

<400> SEQUENCE: 16

Asn Val Asp Phe Thr Val Asp Thr Asn Gly
 1               5                  10

<210> SEQ ID NO 17
<211> LENGTH: 4
<212> TYPE: PRT
<213> ORGANISM: Mus musculus

<400> SEQUENCE: 17

Arg Gly Asp Ser
 1

<210> SEQ ID NO 18
<211> LENGTH: 4
<212> TYPE: PRT
<213> ORGANISM: Artificial Sequence
<220> FEATURE:
<223> OTHER INFORMATION: mutated laminin peptide

<400> SEQUENCE: 18

Arg Gly Glu Ser
 1
```

SCLEROPROTEIN OF AN ADENO-ASSOCIATED VIRUS WITH MODIFIED CHROMATOGRAPHIC PROPERTIES, THE PRODUCTION THEREOF AND USE OF THE SAME

CROSS REFERENCE TO RELATED APPLICATIONS

This application is the U.S. National Stage of International Application No. PCT/EP2000/06861, filed Jul. 18, 2000, which claims benefit of German Application No. 19933719.5, filed Jul. 19, 1999.

The present invention relates to a structural protein of adeno-associated virus which comprises at least one mutation which brings about a modification of the chromatographic properties, to its production and use.

The AAV virus belongs to the family of parvoviruses. These are distinguished by an icosahedral, non-enveloped capsid which has a diameter of 18 to 30 nm and which contains a linear, single-stranded DNA of about 5 kb. Efficient replication of AAV requires coinfection of the host cell with helper viruses, for example with adenoviruses, herpesviruses or vaccinia viruses. In the absence of a helper virus, AAV enters a latent state, the viral genome being capable of stable integration into the host cell genome. The property of AAV integrating into the host genome makes it particularly interesting as a transduction vector for mammalian cells. In general, the two inverted terminal repeats (ITR) which are about 145 bp long are sufficient for the vector functions. They carry the "cis" signals necessary for replication, packaging and integration into the host cell genome. For packaging in recombinant vector particles, a helper plasmid which carries the genes for nonstructural proteins (Rep proteins) and for structural proteins (Cap proteins) is transfected into cells suitable for packaging, for example HeLa or 293 cells, which are then infected, for example, with adenovirus. A lysate containing recombinant AAV particles is obtained after some days. Suitable helper plasmids are described, for example, by Chiorini et al., (1995) Hum. Gene Ther. 6, 1531-1541 or Girod et al. (1999), Nat. Med.

The AAV capsid consists of three different proteins: VP1, VP2 and VP3, whose relative proportions are 5% VP1, 5% VP2 and 90% VP3. The AAV capsid genes are located at the right-hand end of the AAV genome and are encoded by overlapping sequences of the same open reading frame (ORF) using different start codons and two differently spliced transcripts. The VP1 gene contains the whole VP2 gene sequence, which in turn contains the whole VP3 gene sequence with a specific N-terminal region. The fact that the overlapping reading frames code for all three AAV capsid proteins is responsible for the obligatory expression of all capsid proteins, although to different extents.

The molecular masses of the capsid proteins are 87 kD for VP1, 73 kD for VP2 and 62 kD for VP3. The sequences of the capsid genes are described, for example, in Srivastava, A. et al. (1983), J. Virol., 45, 555-564; Muzyczka, N. (1992), Curr. Top. Micro. Immunol., 158, 97-129, Ruffing, N. et al. (1992), J. Virol., 66, 6922-6930 or Rutledge, E. A. et al. (1998) J. Virol. 72, 309-319. The physical and genetic map of the AAV genome is described, for example, in Kotin, R. M. (1994), Human Gene Therapy, 5, 793-801.

Also known are various AAV serotypes, of which the human AAV serotype 2 (AAV2) has been most studied. These analyses showed that AAV viruses possess advantageous properties as viral vectors for somatic gene therapy. The essential advantages are the lack of pathogenicity for humans, the stable integration of viral DNA into the cellular genome, the ability to infect non-dividing cells, the stability of the virion, which makes purification to high titers ($10^{13}$ to $10^{14}$ particles per ml) possible, the low antigenicity, and the absence of viral genes and gene products in the recombinant AAV vector, which is advantageous from the viewpoint of safety for use in gene therapy. The cloning of genes into the AAV vector now takes place by methods generally known to the skilled person, as described, for example, in WO 95/23 867, in Chiorini J. A. et al. (1995), Human Gene Therapy, 6, 1531-1541 or in Kotin, R. M. (1994), supra.

To use AAV as viral transduction vector it is generally necessary to have high titers of recombinant AAV particles. Owing to the fact that there is naturally a relatively small production of particles, one way of achieving high titers is by efficient concentration of the particles. It is also necessary for the particles, especially for in vivo applications, to be as free as possible of impurities which may consist of cellular constituents, DNA, proteins, helper viruses and medium constituents. It is thus necessary to have available an improved purification of AAV particles.

Chromatography is a basic possibility for purification. This physical separation method entails separation of substances by distribution between a stationary and a mobile phase. Chromatography can be divided into two groups on the basis of the physical processes, adsorption chromatography with a solid as stationary phase and partition chromatography with two mutually imiscible phases, and usually mixed forms occur. The separation characteristics of a substance in chromatography depend on its chromatographic properties, in particular its size, its charge, its adsorption behavior, and thus its specific affinity, its hydrophobicity, etc. This means that the chromatographic properties provide a central starting point for achieving via a modification an improvement in the purification and thus, for example, a concentration or greater purity, and a pure modification, for example compared with the wild type, is sufficient to permit a separation and thus better purification.

AAV purification methods, especially by means of chromatography, are described, for example, in WO 97/08298, but no mutation of the AAV structural proteins is. In addition, WO 96/00587 refers to AAV capsid fusion proteins which are said not to interfere with capsid formation and to contain heterologous epitopes of clinically relevant antigens, but the intention is merely to induce an immune response. The publication moreover contains only a general reference to the fusion proteins without giving details on the possible implementation, in particular on suitable insertion sites. However, no alteration of chromatographic properties, in particular for improving the purification, for example by altering the affinities, is described.

It was therefore an object of the present invention to modify the purification properties of the AAV virus, in particular of a structural protein, compared with the wild type.

It has now been found, surprisingly, that structural or capsid proteins of AAV can be modified in such a way that an alteration in the chromatographic properties is brought about thereby.

One aspect of the present invention is therefore an AAV structural protein which comprises at least one mutation which brings about an alteration in the chromatographic properties of the virus. It is preferred in this connection that the alteration in the chromatographic properties makes an improvement in the purification possible, in particular a concentration of the virus, preferably of the virus particles, to higher titers, a purification to greater purity and/or a more efficient purification. The modified chromatographic properties enable, for example, a virus particle purification step to be more specific or efficient as part of a purification which leads to higher particle titers, to purer particles or to more efficient purification. The titer of recombinant particles can be determined, for example, by placing serial dilutions of a particle-containing solution on a membrane and hybridizing this membrane with labeled AAV DNA. Detection of the hybridized DNA allows conclusions to be drawn about the particle concentration, qualitatively or quantitatively depending on the way the test is carried out. The purity of the particles can be determined through the ratio of the structural protein or of the particle proteins to proteins foreign to the particles. Purification is more efficient within the meaning of the present invention if, for example, the purification consists of fewer steps, takes place more quickly or, in particular, is less costly to carry out in an industrial application.

Within the meaning of this invention, an alteration of the chromatographic properties of the virus associated with an improvement in the purification exists, for example, even if the mutation merely brings about a shift in the elution behavior on a chromatography column, that is to say, for example, to lower or higher salt concentrations. It is a general problem of chromatographic purifications that the desired product fractions (e.g. virus particles) and fractions of impurities (other viruses, wild-type viruses, residues of cell lysates, DNA, proteins, in particular serum proteins) are eluted in the same fraction at the same salt content. A targeted mutation according to the invention and the shift in the elution behavior associated therewith results in the fraction with the desired mutated virus particles then eluting no longer with the impure fraction but in a different elution fraction (e.g.—depending on charge—at higher or lower salt concentrations). In some circumstances, but not always, shifts to high salt concentrations, for example through insertion of predominantly positively or negatively charged amino acids or H is TAG into the capsid protein, provide particular advantages because impurities are usually small components and usually elute at lower salt concentrations in conventional purification methods. The capsid mutants then bind better, for example, to the column material and elute later, that is to say at higher salt concentrations. A further desired effect based on the incorporation of charged amino acids is the possibility of loading ion exchangers at a higher salt content, which makes it possible to reduce the amount of column material required, which facilitates manipulation and saves costs in an industrial production method.

It is particularly preferred for the mutation in the structural protein of the invention to bring about a negligible reduction in the infectivity of the virus but, in particular, an increase in the infectivity. Infectivity means for the purpose of this invention the ability to transduce cells.

A further development of this invention is for the modified structural protein to have an increased thermal stability compared with the wild-type AAV. Thus, if the thermal stability is increased, a better thermal inactivation of unwanted other microorganisms or viruses would be possible than is the case for the wild-type AAV. Structural proteins of this type can be found simply by testing a large number of mutants for their thermal stability.

In addition, the modified structural protein is preferably also capable of particle formation, i.e. of forming an icosahedral capsid, especially in the form of an AAV capsid, because particles or capsids are particularly suitable as carriers of selected compounds, e.g. rAAV transduction vectors. The formation of particles can be detected, for example, by electron microscopy. Another detection is the sedimentation behavior during a cesium chloride density gradient centrifugation with subsequent optional detection of viral DNA present in the particles.

It is possible in general for the mutation(s) to be present in the VP1, VP2 and/or VP3 structural protein, with preference for the VP1 and/or the VP3 structural protein. The structural protein may moreover be derived from all AAV serotypes, in particular from human serotypes, preferably from AAV1, AAV2, AAV3, AAV4, AAV5 and/or AAV6, especially from AAV2, AAV3 and/or AAV6.

Said mutation may be a point mutation, a mutation of more than one amino acid, one or more deletion(s), in particular one or more insertion(s) or a combination of said modifications.

In a preferred embodiment, amino acids of a functional sequence are inserted, preferably those which are suitable for affinity chromatography.

Affinity chromatography means a chromatographic method which is based on the ability of certain partners which belong together, such as antigen-antibody, enzyme-substrate, etc., to recognize one another and enter into mutual interaction. Usually one of the partners which belong together is immobilized on a chromatographic sorbent as support, and the specifically appropriate component then binds thereto. Elution then takes place with changed pH, different ionic strength or, for example, analogs of the appropriate component. This also encompasses covalent chromatography, e.g. via formation of disulfide bridges, and hydrophobic chromatography, which hydrophobic interactions are utilized.

The inserted amino acid can, in particular, be selected from the following group: a ligand of a receptor or the receptor of a ligand, an antibody or part of an antibody, in particular an antibody epitope, an antigen or antigen epitope, a hormone, a hormoreceptor, an enzyme, an enzyme substrate, a lectin and/or a sugar-bearing amino acid.

These may preferably be:
a histidine-rich peptide (His TAG), which makes purification on a metal chelate affinity medium possible;
a peptide with more than one charge, which modifies the binding or elution behavior during an ion exchange chromatography and thus makes such a purification step more specific or efficient;
glutathione S-transferase (GST Tag) which makes purification on a glutathione affinity medium possible;
an $F_c$ part of an antibody, which makes purification on a protein A or protein G affinity medium possible;
an immunoglobulin-binding domain, for example protein A or protein G or parts thereof, which makes purification on an affinity medium with an antibody or an $F_c$ part of an antibody possible;
a particular antibody epitope which makes a purification on a medium with coupled antibodies which are specific for the epitope possible;
a lecitin which makes purification on a glycoprotein medium possible;
a nucleic acid binding site which makes purification on nucleic acid media possible;
a heparin binding site which makes purification on a heparin medium possible, the wild-type AAV already having an intrinsic heparin binding site, so that an additional binding site would merely strengthen the binding;
streptavidin which makes purification via biotin or biotinylated proteins possible:

a particular ligand which makes purification on a medium with the appropriate receptor possible or a particular receptor which makes purification on a medium with the appropriate ligand possible.

Preference is likewise given to an integrin, a cytokine or a receptor binding domain of a cytokine, integrin or growth factor, single-chain antibodies which bind to a cell surface receptor, an antibody against cell surface structures, an epitope and/or an antibody-binding structure.

In a preferred embodiment, a peptide with, for example, 5 to 30 amino acids, preferably 8 to 20 amino acids and, in particular, 10 to 18 amino acids is inserted. The peptide has, for example, the sequence QAGTFALRGDNPQG or a sequence which is highly homologous therewith. This particularly preferred ligand is the P1 peptide which is a peptide with a length of 14 amino acids from the core sequence of an alpha chain of the laminin family. This sequence is sufficient, for example, for recognition of an integrin receptor, which mediates inter alia endocytosis of viral particles, e.g. of adenovirus. The P1 peptide binds, irrespective of its conformation (linear or circular), to the integrin receptor. According to the present invention, the coding DNA sequence of the P1 peptide is incorporated into the gene coding for a structural protein of AAV which is located, for example on a helper plasmid. Packaging with the mutant helper plasmid results in recombinant AAV with P1 in the capsid (rAAV-P1). It was possible to show for insertion of this peptide that these AAV particles are eluted from a cation exchanger at lower conductivity compared with unmodified AAV particles, and so permits improved separation (e.g. from the wild type) and purification, depending on the conditions.

A particularly preferred structural protein of the invention is one which comprises at least one other mutation. By this is meant that the structural protein comprises not only a mutation which brings about a modification of the chromatographic properties of the virus but also another mutation which does not necessarily also bring about a modification of the chromatographic properties of the virus. A particularly preferred other mutation in this case is one which brings about an alteration, preferably increase, in the infectivity of the virus.

A further preferred aspect of the present invention is an AAV structural protein in which the other mutation(s) bring(s) about a reduction in the antigenicity.

Antigenicity means for the purpose of this invention the induction of both antibody formation and binding on the basis of the immune system. The term also encompasses immunogenicity, that is to say the induction of an immune response. The reduction in antigenicity therefore means the reduction in antibody formation and binding both by reducing the antigenic epitopes and by reducing the antigenic effect of particular epitopes or by modification and deletion of certain epitopes present in the wild type. The modified antigenicity may moreover relate both to the humoral and to the cellular immune response.

In a further preferred embodiment, the other mutation(s) represent(s) one or more deletions and/or one or more insertions in the structural protein or combinations of said modifications. In this connection, insertion is preferably the insertion of a cell membrane receptor ligand, of a Rep protein or peptide, for example in the form of a Rep domain, of an immunosuppressive protein or peptide and/or of a protein or peptide with a signal for double strand synthesis of a transgene or foreign gene. A preferred example in this connection is the P1 peptide (QAGTFALRGDNPQG)(SEQ ID NO: 1) (see above).

Examples of insertions for the other mutation are, inter alia, integrins, cytokines, or receptor binding domains of cytokines, integrins or growth factors such as, for example, GM-CSF, IL-2, IL-12, CD40L, TNF, NGF, PDGF or EGF, single-chain antibodies which bind to cell surface receptors, so-called single chain antibodies (scFv), single-chain antibodies which bind for example to the surface receptors CD40, CD40L, B7, CD28 or CD34, or epitopes or receptor binding sites which in turn are recognized, for example, by particular antibodies, for example anti-CD40L monoclonal antibodies, or by chemical substances or hormones, e.g. catecholamines.

In a preferred embodiment of the other mutation there is insertion of antibody-binding structures such as, for example, protein A, protein G or anti-Fc-antibody, or parts thereof. To the latter in turn are coupled specific antibodies against particular cell surface structures (for example against CD40 in the case of lymphatic cells or against CD34 in the case of hematopoietic cells).

The mutation(s) is(are) preferably located on the virus surface. To determine the structural protein regions located on the surface, it has surprisingly been found according to the present invention that CPV and AAV2 sequences and structures are comparable. It is therefore possible to have recourse preferably to known crystal structures of parvoviruses such as of parvovirus B19 or of CPV (canine parvovirus) and to identify with the aid of homology comparisons protein domains located on the virus surface. According to the present invention, therefore, for example a computer-assisted comparison between CPV and AAV2, and parvovirus B19 and AAV2, has surprisingly resulted in reproducible identification of loops in VP3 whose sequence varies, i.e. which have low homology and which are presumed to be located on the virus surface. Since the antigens for the humoral immune response must be accessible for antibodies and thus be on the virus surface, these loops represent preferred candidates for mutations. Thus, the known crystal structure of the CPV VP2 capsid proteins (e.g. Luo M. (1988), J. Mol. Biol., 200, 209-211; Wu and Rossmann (1993), J. Mol. Biol., 233, 231-244) was, because of the great similarity to the AAV2 VP3 in the secondary structure of the protein, taken as pattern for finding the regions exposed on the viral capsid surface and sufficiently flexible, because of the local amino acid sequence, to withstand for example the insertion of a peptide sequence. Care was taken in this connection not to select any capsid-destabilizing secondary structural elements of the AAV2 capsid protein.

In a preferred embodiment, the mutation(s) are located at the N terminus of the structural protein, because it has been found that, for example in the parvoviruses CPV and B19, the N terminus is located on the cell surface.

A further possibility for determining structural protein regions located on the surface is to compare the capsid-encoding nucleic acid sequences of different AAV serotypes. It is possible to use for this purpose for example known DNA sequences of different AAV serotypes, such as AAV1, AAV2, AAV3, AAV4, AAV5 or AAV6, for structural analyses of possible capsid morphologies of, for example, AAV2, it being possible to calculate ab initio possible tertiary structures and assign sequence regions to the inner or outer capsid regions on the basis of generally known amino acid properties. It was thus possible according to the present invention for example to find in the VP3 region of the AAV2 capsid possible insertion sites which made it possible to insert, for example, peptides and express them on the virus surface (see below).

In a preferred embodiment, the mutation(s) is(are) brought about by one or more insertions in the XhoI cleavage sites of the VP1-encoding nucleic acid and, in another preferred embodiment, in the BsrBI cleavage site of the VP1-encoding nucleic acid. Another preferred embodiment of the structural protein of the invention is generated by a deletion between the BsrBI-HindIII cleavage sites of the VP1-encoding nucleic acid and one or more insertions, preferably at the deletion site.

In another preferred embodiment of the present invention, the mutation(s) is(are) brought about by one or more deletions between the XhoI-XhoI cleavage sites of the VP1-encoding nucleic acid which comprises 62 amino acids (Hermonat, P. L. et al. (1984), J. Virol., 51, 329-339). In another preferred and corresponding embodiment, the deletion(s) is located between the BsrBI-HindIII cleavage sites of the VP1-encoding nucleic acid which is located within the deletion described above and comprises 29 amino acids. This deletion has the advantage that it has no overlap with the rep gene and therefore has a negligible effect on the packaging mechanism.

In another preferred embodiment, one or more insertions are present in the VP3 structural protein (Rutledge, E. A. et al. (1998) supra) before and/or after at least one amino acid in the sequence selected from YKQIS SQSGA (SEQ ID NO: 2), YLTLN NGSQA (SEQ ID NO: 3), YYLSR TNTPS (SEQ ID NO: 4), EEKFF PQSGV (SEQ ID NO: 5), NPVAT (SEQ ID NO: 6), EQYGS (SEQ ID NO: 7), LQRGN RQAAT (SEQ ID NO: 8), NVDFT VDTNG (SEQ ID NO: 9), because these sites are located on the exposed sites of a loop, in which case the risk of altering the VP3 structure is small.

The point mutation(s), the mutation(s) of more than one amino acid, the deletion(s) or insertion(s) is/are carried out by deletion and insertion by generally known methods in the gene coding for the structural protein. The deletions can be introduced into the individual structural protein genes for example by PCR-assisted mutagenesis. The insertions can be introduced by generally known methods, for example by hydrolysis by restriction endonucleases of the appropriate structural protein genes and subsequent ligase reaction. Subsequent expression of the mutated gene leads to the structural protein of the invention.

Another aspect of the present invention is also a structural protein of the invention in the form of an AAV particle, in particular in the form of an AAV capsid, because particles and capsids are particularly suitable as carriers of selected compounds, e.g. rAAV transduction vectors.

Further aspects of the present invention are a nucleic acid, preferably an RNA or a DNA, in particular a double-stranded DNA, coding for a structural protein of the invention.

The present invention also relates to a cell, preferably a mammalian cell, for example a COS cell, HeLa cell or 293 cell, comprising a nucleic acid of the invention. Cells of these types are suitable, for example, for producing the recombinant AAV particles.

A further aspect of the present invention is therefore also a method for producing a structural protein of the invention, in particular for producing a structural protein of the invention in the form of an AAV particle, where a suitable cell comprising a nucleic acid coding for the structural protein of the invention is cultivated and, where appropriate, the expressed structural protein is isolated. The structural protein of the invention can be purified and isolated for example by chromatography.

Another aspect of the present invention relates to a pharmaceutical comprising a structural protein of the invention, a nucleic acid of the invention and/or a cell of the invention and, where appropriate, suitable excipients and additives, such as, for example, a physiological saline solution, stabilizers, proteinase inhibitors, DNAse inhibitors, etc.

A further aspect of the present invention relates to the use of the structural protein of the invention, of a nucleic acid of the invention or of a cell of the invention for the purification of AAV and AAV particles, for altering the tropism of AAV, for altering the antigenicity of AAV, for transforming a cell, in particular a cell whose susceptibility to an AAV infection was previously low, such as, for example, a hematopoetic cell, for genomic targeting, for diagnosis, for activity investigations and/or—in the form of suitable rAAV vectors—for gene therapy. By gene therapy is meant a type of therapy in which an effector gene, usually a protein, is expressed through the introduction of nucleic acids into cells. A distinction is made in principle between in vitro and in vivo methods. In in vitro methods, cells are removed from the organism and transduced ex vivo with vectors in order subsequently to be introduced again into the same or a different organism. In vivo gene therapy involves vectors being administered, for example for controlling tumors, systemically (e.g. via the bloodstream) or directly into the tumor, the tissue or the organs.

A considerable advantage of the present invention is that the mutagenesis according to the invention of AAV structural proteins makes it possible, by modifying the chromatographic properties, to create new possibilities for more specific purification methods essentially without loss of the efficiency of packaging of recombinant AAV vectors in the capsid of the virus. This creates the conditions for purifying AAV or AAV particles to higher titers and/or greater purity and making the purification more efficient and cost effective. This in turn makes industrial application of recombinant AAV possible for cell transformations and gene therapies on the commercial scale.

The following figures and examples are intended to illustrate the invention in detail without restricting it.

DESCRIPTION OF THE FIGURES

FIG. 1 shows the chromatogram of a wild-type AAV sample in one run through a POROS 50HS cation exchange column. The flow-through volume is plotted against the conductivity (left-hand y axis) and against the absorption at 280 nm (right-hand y axis). The AAV particles are eluted in fractions 12 and 13, which corresponds to an average conductivity of 30 mS/cm (300 mm NaCl) (see thick horizontal line).

FIG. 2 shows the chromatogram of an AAV sample consisting of mutated AAV particles (insertion of the peptide QAGTFALRGDNPQG after amino acid 587; I-587 in example 3) in one run through a POROS 50HS cation exchange column. The flow-through volume is plotted against the conductivity (left-hand y axis) and against the absorption at 280 nm (right-hand y axis). The modified AAV particles eluted in fractions 6 and 7, which corresponds to an average conductivity of 22 mS/cm (220 mM NaCl) (see thick horizontal line).

EXAMPLES

Example 1

The following mutations were produced by PCR-assisted mutagenesis and cutting with the restriction enzymes XhoI, BsrBI and HindIII:

Mutations in VP1
  a) Deletion between the XhoI-XhoI cleavage sites of VP-1 (ΔXho; 62 amino acids, AA) (Hermonat et al. (1984) Journal of Virology 51, 329-339),
  b) Deletion between BsrBI and HindIII cleavage sites of VP-1, which is located within the above deletion a) and comprises 29 AA (ΔBH);
  c) Deletion between BsrBI and HindIII, and insertion of a ligand (P1 peptide) (ΔBH+L); and
  d) Pure insertion of the ligand (P1 peptide) at the BsrBI cleavage site (B+L).

Mutations in VP3

| | | |
|---|---|---|
| a) | ins261; YKQIS SQSGA | (SEQ ID NO: 2) |
| b) | ins381; YLTLN NGSQA | (SEQ ID NO: 3) |
| c) | ins447; YYLSR TNTPS | (SEQ ID NO: 4) |
| d) | ins534; EEKFF PQSGV | (SEQ ID NO: 5) |
| e) | ins573; NPVAT EQYGS | (SEQ ID NO: 14) |
| f) | ins587; LQRGN RQAAT | (SEQ ID NO: 8) |
| g) | ins713; NVDFT VDTNG | (SEQ ID NO: 9) |

(Named according to the number of amino acids (AA) counted after the AA from the start of the N terminus in VP-1 of AAV2, flanked by in each case 5 amino acids located N-terminal thereof and 5 amino acids located C-terminal thereof; the AA after which the insertion has been introduced is shown in bold script).

It is also possible likewise to introduce an insertion into the five directly adjacent AA which are located next to the AA in bold, because these are likewise located inside a loop in the AAV2 capsid.

Example 2

Characterization of the Capsid Mutants

After carrying out the mutations in the AAV2 genome and packaging the mutated viruses with LacZ reporter gene, the physical vector titers were determined by dot-blot and capsid titer with A20 antibody ELISA, and initial infection tests were carried out on HeLa cells. It was thus possible to determine whether the mutations impair the structure of the VP proteins or the interaction between various VP proteins in such a way that packaging is impaired or suppressed (table 1).

TABLE 1

Packaging efficiency for the produced virus mutants

| | Genomic virus titer | Caspid titer (ELISA with A20 MAb) |
|---|---|---|
| Virus stock | | |
| Wild-type capsid | $1 \cdot 10^{12}$ | $1 \cdot 10^{11}$ |
| VP1 mutants | | |
| Δxho | $6 \cdot 10^{12}$ | $5 \cdot 10^{10}$ |
| ΔBH | $8 \cdot 10^{11}$ | $4 \cdot 10^{9}$ |
| ΔBH + L | $1 \cdot 10^{13}$ | $5 \cdot 10^{10}$ |
| B + L | $3 \cdot 10^{12}$ | $5 \cdot 10^{9}$ |
| VP3 mutants | | |
| ins261 | $1 \cdot 10^{10}$ | $<10^{8}$ |
| ins381 | $3 \cdot 10^{10}$ | $<10^{8}$ |
| ins447 | $1 \cdot 10^{12}$ | $4 \cdot 10^{10}$ |
| ins534 | $1 \cdot 10^{10}$ | $<10^{8}$ |
| ins573 | $3 \cdot 10^{10}$ | $<10^{8}$ |

TABLE 1-continued

Packaging efficiency for the produced virus mutants

| | Genomic virus titer | Caspid titer (ELISA with A20 MAb) |
|---|---|---|
| ins587 | $1 \cdot 10^{12}$ | $2 \cdot 10^{10}$ |
| ins713 | $5 \cdot 10^{10}$ | $<10^{8}$ |

The genomic virus titers (dot-blot) and capsid titers (A20 capsid ELISA) are shown. The concentrations are stated in particles/ml.

It was possible to show for all 4 VP1 mutants that mutations have no effect on the packaging efficiency, and all the mutated viruses can be packaged with similar titers as good as those for vectors with unmutated capsid ($10^{11}$ to $10^{13}$ genomic particles/ml). It was also possible for the AAV vectors with mutations in the VP3 region to be packaged successfully ($10^{10}$-$10^{12}$ genomic particles/ml).

Example 3

P1 Mutation in VP3

The starting point was a plasmid pUC-AV2 which was produced by subcloning the 4.8 kb BglII fragment of pAV2 (ATCC 37261, ref. 53) into the BamHI cleavage site of pUC19 (New England BioLabs Inc.). Mutations were carried out at defined sites in the plasmid by means of the PCR-assisted mutagenesis known to the skilled worker. This involved insertion of a sequence coding for P1, a 14 AA peptide with the AA sequence QAGTFALRGDNPQG, which contains the RGD binding motif of a laminin fragment (Aumailly et al. (1990) FEBS Lett. 262, 82-86), after nucleotides 2985, 3543 and 3963. This corresponds to an insertion after amino acids 261, 447 and 587 in the AAV2 capsid protein (named according to the number of amino acids (AA) counted after the AA from the start of the N terminus in VP-1 of AAV2). In the subsequent PCR, in each case 2 mutation-specific primers are used, and a plasmid, pCap, which contains only the cap gene and is formed by cutting the 2.2 kb EcoRI-BspMI fragment out of pUC-Av2 and inserting it into the EcoRI cleavage site of pUC19, is used as template. The PCR products are subsequently amplified in bacteria and sequenced, and the 1.4 kb EcoNI-XcmI fragment which contains P1 is subcloned in pUC-AV2 in which the corresponding wild-type cap sequence has been cut out. Consequently, the plasmids (mutants) which are named after the AA insertion sites pI-261, pI-381, pI-447 and pI-587 contained the complete AAV2 genome. The corresponding mutated proteins are referred to as I-261, I-381, I-447 and I-587.

Example 4

Production of AAV2 Particles

HeLa cells (a human cervical epithelial cell line) were transfected with the plasmids of example 1, incubated for about 20 h and then infected with adenovirus type 5. 72 h after the infection, the cells were disrupted and the AAV2 particles were purified on a CsCl gradient.

Example 5

Characterization of the Capsid Mutants of Example 3

The intention of these experiments was to establish whether the capsid mutants are able to package the viral genome and form complete capsids. AAV2 particles of the mutants of example 4 were examined to find whether and, if yes, how many particles carry the viral genome and how much DNA was packaged in the capsid mutants. For this purpose, the virus particles (mutants and wild type) purified in example 4 were treated with DNAse, blotted and hybridized with a Rep probe.

The titer which emerged from this showed no quantitative or qualitative difference from the wild type (see table 2). The viruses retained the ability to package the genome.

It was further possible to confirm by electron microscopic analysis that the capsid is also formed.

The mutations were therefore not carried out in regions which are important for correct folding, capsid assembly or packaging of the genome. The function of the AAV particles of the invention is unimpaired.

In order to be able to infer whether the mutated capsids are completely formed and show no change in antigenicity, A20 monoclonal antibodies (A20 MAb) were employed in an ELISA in a further experiment. A20 MAb reacts specifically with the completely assembled AAV2 capsid of the wild type (Wistuba et al., (1997), J. Virol. 71, 1341-1352). Once again, the results are shown in table 2. It emerges from this that capsid formation is not impaired by the insertion in the mutants I-447 and I-587, whereas the A20 monoclonal antibody no longer binds in the case of I-261, but, because the examination under the electron microscope shows that the capsids are nevertheless formed, this is attributable to a modification of the antigenicity.

TABLE 2

Packaging efficiency and antigenicity of the virus mutants produced in example 3

|  | Genomic virus titer | (ELISA with A20 MAb) |
| --- | --- | --- |
| Virus stock |  |  |
| Wild-type capsid | $8 \cdot 10^{13}$ | $6 \cdot 10^{12}$ |
| Mutants |  |  |
| I-261 | $1 \cdot 10^{12}$ | n.m. |
| I-381 | $1 \cdot 10^{12}$ | n.m. |
| I-447 | $1 \cdot 10^{13}$ | $8 \cdot 10^{11}$ |
| I-587 | $4 \cdot 10^{13}$ | $3 \cdot 10^{12}$ |

The genomic virus titers (dot-blot) and the titer with A20 capsid ELISA are shown. The concentrations are stated in particles/ml. "n.m." means "not measurable".

Example 6

Modified Elution Behavior of the Capsid Mutants

Recombinant wild-type AAV (in 20 mM Hepes pH 6.8, 100 mM NaCl, 2 mM $MgCl_2$) were loaded onto a 0.8 ml POROS 20HS cationic exchanger column (Perkin-Elmer, Weiterstadt). An Äkta system (Pharmacia) was used to apply a gradient of 30 column volumes from 100 to 700 mM NaCl in 20 mM Hepes [lacuna] 6.8. Western blot analysis showed that AAV eluted in fractions 12 and 13, which corresponds to elution of wild-type AAV at 30 mS/cm (=about 300 mM NaCl) (see FIG. 1).

A capsid mutant (I-587 from example 3) of AAV (the P1 peptide QAGTFALRGDNPQG is inserted after amino acid 587; in PBS, pH 6.8) was loaded onto the same 0.8 ml POROS 20 HS cation exchanger column (see above). A gradient of 30 column volumes 50-1000 mM NaCl in 20 mM Hepes pH 6.8 in an Äkta system was used for elution. The AAV mutant was present according to Western blot analysis in fractions 6 and 7. This corresponds to elution of about 22 ms/cm (=about 220 mM NaCl) (see FIG. 2).

Figure 1:
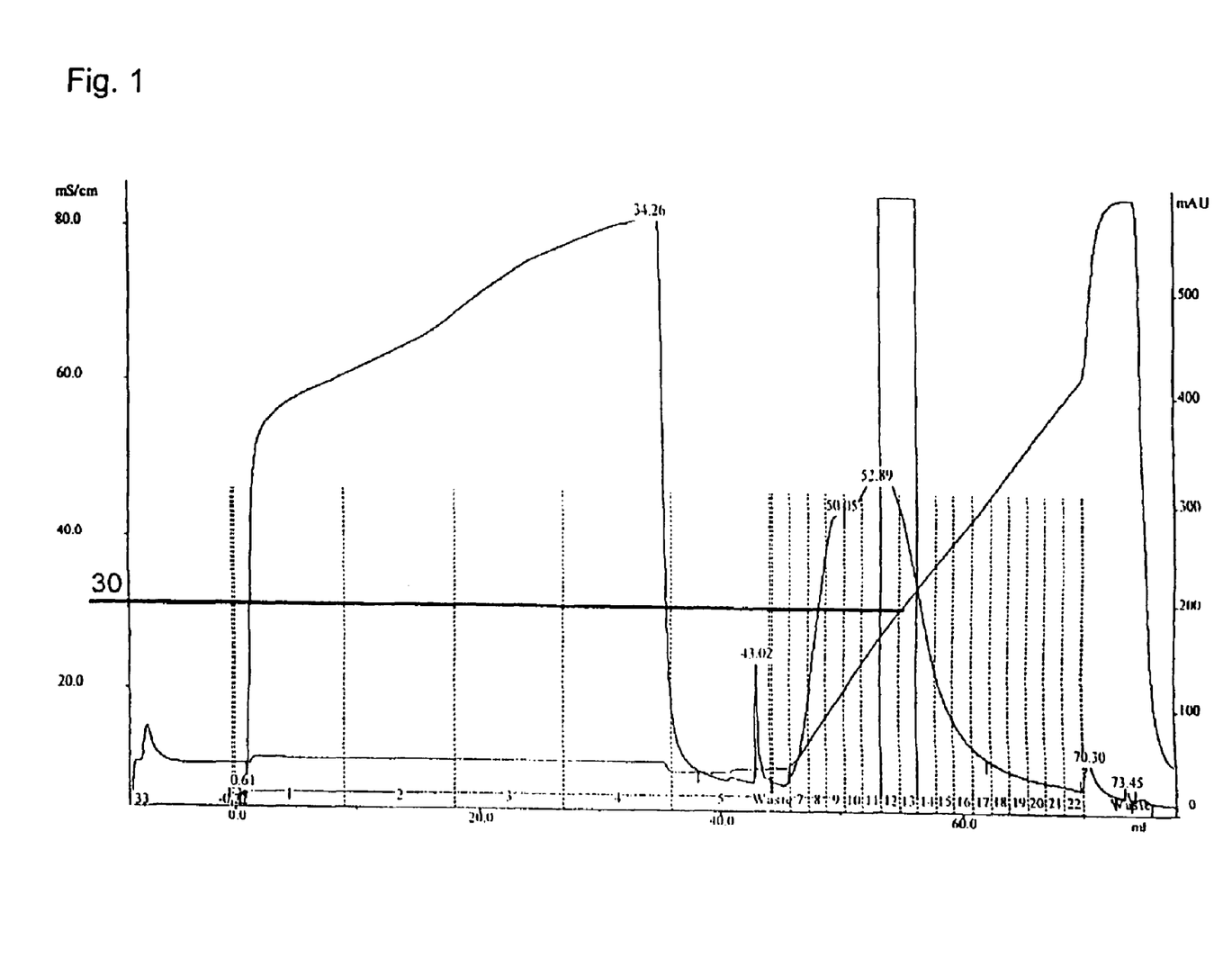
Figure 2:
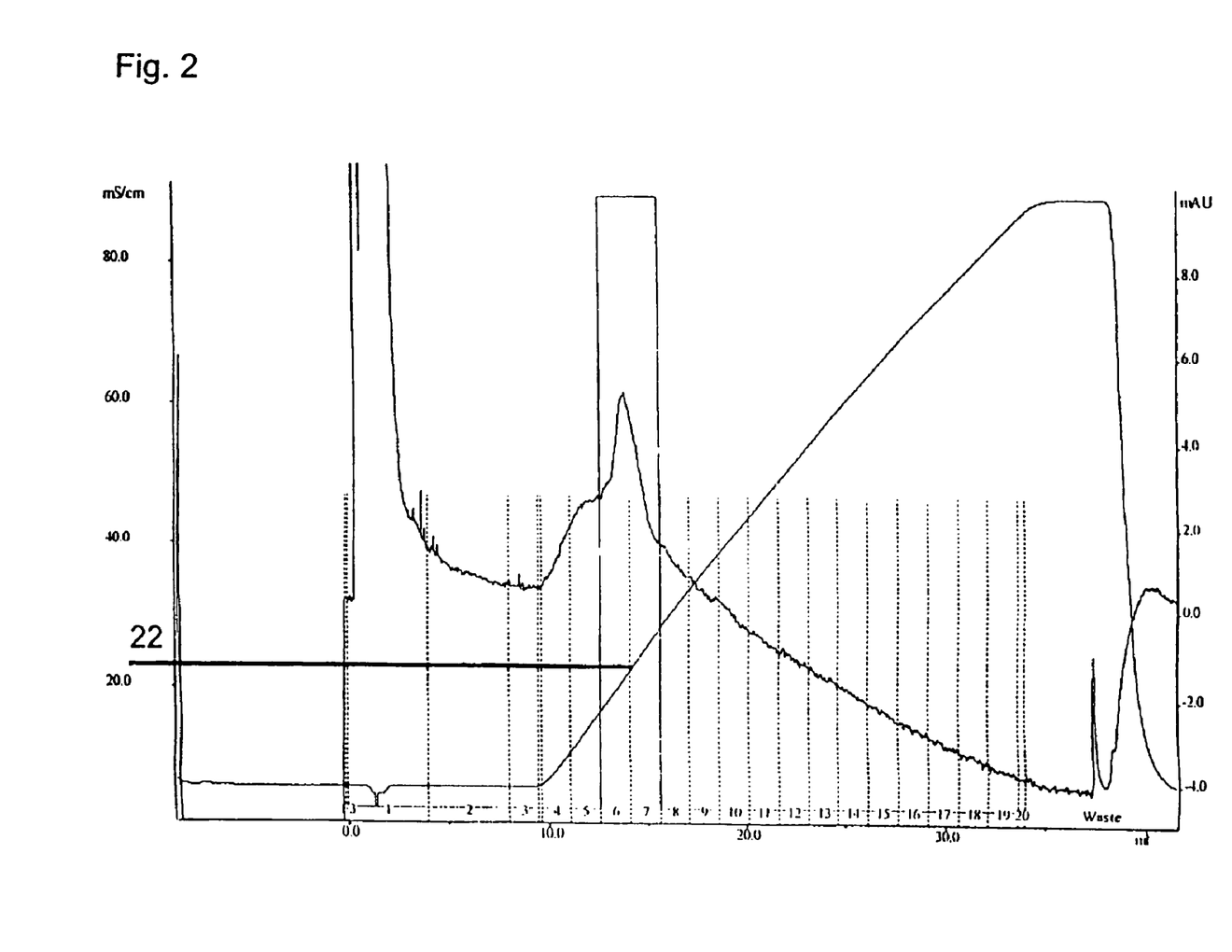

This shows that insertion of the QAGTFALRGDNPQG (SEQ ID NO: 1) peptide alters the elution behavior of the AAV particles so that, at the same pH, the mutated particles elute at a lower salt concentration than the wild-type particles. This means that the virus fraction is shifted toward other fractions which are in some circumstances less impure or otherwise more suitable. It is therefore possible to alter the chromatographic properties of the AAV particles by insertions, deletions or other modifications of the capsid proteins. It is possible in particular in one variant of the insertion shown to construct, by introducing amino acids with a predominantly positive charge, for example at the insertion sites shown in the examples, capsid mutants of the invention which elute at higher salt concentrations compared with the wild type (which elutes in a broad, less impure peak). The affinity of the mutant for the column material is enhanced thereby, so that elution does not take place until the salt concentrations are high, that is to say in regions which are normally less contaminated by smaller foreign proteins.

Example 7

Infection Tests with Mutants of Example 3

In order to test the tropism of the capsid mutants I-261, I-381, I-447 and I-587, the cell lines Co-115 and B16F10 were infected with the mutated viruses. Co-115 cells were used to test the wild-type receptor tropism of the virions because the latter can be transduced with wild-type AAV2 and do not bind the P1 peptide. The B16F10 cell line was used for the reasons already mentioned in example 9. Three days after the infection, the cells were investigated by immunofluorescence measurement using an anti-Rep antibody to find whether the viral Rep protein is expressed (Wistuba et al. (1997) J. Virol. 71, 1341-1352; Wistuba et al. (1995) J. Virol. 69, 5311-5319). Cells were grown to 70% confluence on microscope slides and incubated with various concentrations of viral preparations of the invention in serum-free medium together with adenovirus 5. The titers of the viral preparations were determined three days later by in situ detection of Rep protein synthesis in an immunofluorescence assay (Rep titer). The immuno-fluorescence staining was carried out in this case with AAV2-infected cells by a method of Wistuba et al. (Wistuba et al. (1997) J. Virol. 71, 1341-1352; Wistuba et al. (1995) J. Virol. 69, 5311-5319). The microscope slides were washed once with PBS, fixed in methanol (5 min, 4° C.) and then treated with acetone (5 min, 4° C.). The cells were then incubated with the monoclonal antibody 76-3, which reacts with Rep proteins of AAV2, at room temperature for one hour. This was followed by washing and incubation with a rhodamine-conjugated anti-mouse secondary antibody at a dilution of 1:50 in PBS with 1% BSA for one hour. The titers were calculated from the last limiting dilution of the viral stock solution which led to fluorescence-positive cells.

Rep-positive CO115 cells were detectable after infection with wild-type AAV2 and with mutants I-261, I-447 and I-587. In Co115 cells, the infectivity of I-261, I-587 and I-447 was two to three orders of magnitude smaller than that of the wild type (table 3). Transfection of B16F10 cells with I-447 was just as inefficient as with wild-type virus (table 3). In clear contrast with this, Rep-positive B16F10 cells are detectable after infection with I-587, and the titer determined for the I-587 virus was $1\times10^6$ Rep EFU/ml (table 3).

In order to investigate whether the transfection of B16F10 cells by the mutant I-587 was mediated specifically by the interaction between the P1 sequence on the surface of the mutated capsid and the integrin receptor on the surface of the B16F10 cells, the cells were incubated either with the competing RGDS or with the inactive RGES peptide at concentrations of 200 μmol before infection with the virus. Addition of RGDS peptide neutralized the infectivity of I-587 for B16F10 cells (table 3), whereas the control peptide RGES had no effect.

TABLE 3

| | Virus titer on the cell surface | | |
|---|---|---|---|
| | Titer on | Titer on B16F10 cells | |
| | CO115 cells | − RGDS | + RGDS |
| Virus stock | | | |
| Wild-type caspid | $2 \cdot 10^9$ | <1 | Nd |
| Mutants | | | |
| I-261 | $7 \cdot 10^6$ | nd | Nd |
| I-381 | n.m. | nd | Nd |
| I-447 | $1 \cdot 10^6$ | <1 | Nd |
| I-587 | $1 \cdot 10^7$ | $1 \cdot 10^6$ | <1 |

TABLE 3-continued

| | Virus titer on the cell surface | | |
|---|---|---|---|
| | Titer on | Titer on B16F10 cells | |
| | CO115 cells | − RGDS | + RGDS |
| rAAV/LacZ | $5 \cdot 10^7$ | <1 | Nd |
| rAAV(I-587)/LacZ | $6 \cdot 10^5$ | $5 \cdot 10^4$ | <1 |

The titers for the wild type-susceptible CO115 cells and the wild type-resistant B16F10 cells are shown. The titers are expressed in Rep EFU/ml for I-447 and I-587, as for the wild type, and in LacZ EFU/ml for rAAV/LacZ and rAAV(I-587)/LacZ. EFU here means expression-forming units (expressing forming unit) and nd means "not determined". "n.m." means "not measurable".

Example 8

Infection Assay of the Mutants of Example 3 with Galactosidase

In another experiment based on example 6, rAAV vectors containing either the wild type (rAAV virion) or I-587 (rAAV(I-587) virion) were produced with a LacZ reporter gene. The viral preparations were called rAAV/LacZ and rAAV(I-587)/LacZ and used for infection of B16F10 and CO115 cells (controls).

Infected cells were assayed for β-galactosidase expression by X-Gal staining three days after the infection. This entailed use of the X-Gal in situ assay for cytochemical staining (LacZ titer). After this, the cells were, in order to assay the expression of β-galactosidase, washed once in PBS and then fixed with 1.5% glutaraldehyde. The cells were then treated with X-Gal (5-bromo-4-chloro-3-indolyl-β-D-galacto-pyranoside) as already described by Chiorini et al. (1995) Hum. Gen. Ther. 6, 1531-1541. The titers were calculated from the last limiting dilution of the viral stock solution which led to β-galactosidase-producing cells.

Both virions were infectious for the CO115 control cells, although rAAV (I-587)/LacZ was less efficient by 2 orders of magnitude. With type B16F10—as expected—no β-galactosidase-positive cells were found after infection with rAAV/LacZ. By contrast, surprisingly, a markedly large number of β-galactosidase-positive cells were found after infection with rAAV(I-587)/LacZ. The titer determined for rAAV-(I-587)/LacZ was $5\times10^4$ LacZ EFU per ml. The infectivity of rAAV vectors for B16F10 cells was improved by more than four orders of magnitude by the mutation according to the invention (table 3).

The invention claimed is:

1. A method for purifying AAV particles, said method comprising providing AAV particles having a structural protein of adeno-associated virus (AAV) that comprises at least one insertion in VP3 located directly adjacent to an amino acid in the sequence selected from the group consisting of YKQIS SQSGA (SEQ ID NO: 2), YLTLN NGSQA (SEQ ID NO: 3), YYLSR TNTPS (SEQ ID NO: 4), EEKFF PQSGV (SEQ ID NO: 5), NPVAT EQYGS (SEQ ID NO: 14), LQRGN RQAAT (SEQ ID NO: 8), and NVDFT VDTNG (SEQ ID NO: 9), wherein said insertion brings about an alteration in the chromatographic properties of the virus; and purifying said AAV particles.

2. The method as claimed in claim 1, wherein the alteration in the chromatographic properties makes possible an improvement in the purification relative to purification of wild-type AAV, the improvement being selected from the group consisting of a concentration of the virus to higher titers, a concentration of the virus particles to higher titers, a purification to greater purity, and a more efficient purification.

3. The method as claimed in claim 1, wherein the insertion brings about a negligible reduction in the infectivity of the virus.

4. The method as claimed in claim 1, wherein the structural protein is derived from the group consisting of AAV1, AAV2, AAV3, AAV4, AAV5, AAV6, and other AAV serotypes derived therefrom.

5. The method as claimed in claim 1, wherein the insertion comprises an inserted amino acid sequence selected from the group consisting of a ligand of a receptor, the receptor of a ligand, an antibody, part of an antibody, an antibody epitope, an antigen, an antigen epitope, a hormone, a hormone receptor, an enzyme, an enzyme substrate, a lectin, sugar-bearing amino acids, sugar-bearing amino acids from a histidine-rich peptide (H is tag), a multiply charged peptide, glutathione S-transferase (GST tag), an $F_c$ part of an antibody, an immunoglobulin-binding domain, protein A, protein G, an immunoglobulin-binding domain of protein A, an immunoglobulin-binding domain part of protein G, a nucleic acid binding site, a heparin binding site, a specific ligand, a specific receptor, an integrin, a cytokine, a receptor binding domain of a cytokine, a growth factor, single-chain antibodies which bind to a cell surface receptor, an antibody against cell surface structures, an epitope, and an antibody-binding structure.

6. The method as claimed in claim 1, wherein a peptide which has the sequence QAGTFALRGDNPQG (SEQ ID NO: 1) is inserted into the structural protein.

7. The method as claimed in claim 1, wherein the insertion is located directly adjacent to an amino acid in the sequence YKQIS SQSGA (SEQ ID NO: 2).

8. The method as claimed in claim 5, wherein the inserted amino acid sequence is between 5 and 30 amino acids in length.

9. The method as claimed in claim 1, wherein the insertion is located directly adjacent to an amino acid in the sequence YLTLN NGSQA (SEQ ID NO: 3).

10. The method as claimed in claim 1, wherein the insertion is located directly adjacent to an amino acid in the sequence YYLSR TNTPS (SEQ ID NO: 4).

11. The method as claimed in claim 1, wherein the insertion is located directly adjacent to an amino acid in the sequence EEKFF PQSGV (SEQ ID NO: 5).

12. The method as claimed in claim 1, wherein the insertion is located directly adjacent to an amino acid in the sequence NPVAT EQYGS (SEQ ID NO: 14).

13. The method as claimed in claim 1, wherein the insertion is located directly adjacent to an amino acid in the sequence LQRGN RQAAT (SEQ ID NO: 8).

14. The method as claimed in claim 1, wherein the insertion is located directly adjacent to an amino acid in the sequence NVDFT VDTNG (SEQ ID NO: 9).

15. The method as claimed in claim 1, wherein the structural protein comprises at least one other mutation.

16. The method as claimed in claim 15, wherein the other mutation(s) in the structural protein bring(s) about an alteration in the infectivity of the virus.

17. The method as claimed in claim 15, wherein the other mutation(s) in the structural protein bring(s) about a reduction in the antigenicity of the virus.

18. The method as claimed in claim 15, wherein the other mutation(s) in the structural protein is/are selected from the group consisting of one or more deletion(s), one or more insertion(s), and a combination of said modifications.

19. The method as claimed in claim 15, wherein the other mutation(s) is/are an insertion into the structural protein that is selected from the group consisting of a cell membrane receptor ligand, a Rep protein, a Rep peptide, an immunosuppressive protein, an immunosuppressive peptide, a protein with a signal for double strand synthesis of the foreign gene, and a peptide with a signal for double strand synthesis of the foreign gene.

20. The method as claimed in claim 15, wherein the other mutation(s) is/are an insertion into the structural protein that is selected from the group consisting of an integrin, a cytokine, a receptor binding domain of a cytokine, a growth factor, single-chain antibodies which bind to a cell surface receptor, an antibody against cell surface structures, an antibody-binding structure, and an epitope.

21. The method as claimed in claim 15, wherein the additional mutation(s) in the structural protein is/are located on the virus surface.

22. The method as claimed in claim 15, wherein the additional mutation(s) is/are located at the N terminus of the structural protein.

23. The method as claimed in claim 15, wherein the additional mutation(s) in the structural protein is/are brought about by one or more insertions in the XhoI cleavage site of the VP1-encoding nucleic acid.

24. The method as claimed in claim 15, wherein the additional mutation(s) in the structural protein is/are brought about by one or more insertions in the BsrBI cleavage site of the VP1-encoding nucleic acid.

25. The method as claimed in claim 15, wherein the additional mutation(s) in the structural protein is/are brought about by one or more deletions between the BsrBI-HindIII cleavage sites of the VP1-encoding nucleic acid, and one or more insertions.

26. The method as claimed in claim 15, wherein the additional mutation(s) in the structural protein is/are brought about by one or more deletions between the XhoI-XhoI cleavage sites of the VP1-encoding nucleic acid.

27. The method as claimed in claim 15, wherein the additional mutation(s) is/are brought about by one or more deletions between the BsrBI-HindIII cleavage sites of the VP1-encoding nucleic acid.

28. The method as claimed in claim 15, wherein one or more additional insertion(s) in VP3 is/are located directly adjacent to an amino acid in the sequence selected from the group consisting of YKQIS SQSGA (SEQ ID NO: 2), YLTLN NGSQA (SEQ ID NO: 3), YYLSR TNTPS (SEQ ID NO: 4), EEKFF PQSGV (SEQ ID NO: 5), NPVAT EQYGS (SEQ ID NO: 14), LQRGN RQAAT (SEQ ID NO: 8), and NVDFT VDTNG (SEQ ID NO: 9).

* * * * *